United States Patent [19]

Riiber

[11] 3,981,934

[45] Sept. 21, 1976

[54] METHOD FOR DRYING TRINITROTOLUENE

[75] Inventor: Odd Riiber, Gullaug pr. Drammen, Norway

[73] Assignee: Dyno Industrier A.S., Oslo, Norway

[22] Filed: Sept. 19, 1974

[21] Appl. No.: 507,781

[30] Foreign Application Priority Data

Sept. 20, 1973 Norway .............................. 3698/73

[52] U.S. Cl. .................................. 260/645; 23/266; 34/34; 260/704

[51] Int. Cl.$^{2}$ ...................... C07C 79/10; F26B 7/00

[58] Field of Search ................. 260/645, 704; 34/34

[56] References Cited

UNITED STATES PATENTS 1,605,839 11/1926 Herman ................................. 34/34

OTHER PUBLICATIONS

Urbanski, Chemistry and Technology of Explosives, vol. 1, The MacMillan Co., New York, 1964, pp. 379 and 380.

*Primary Examiner*—Leland A. Sebastian
*Attorney, Agent, or Firm*—Wenderoth, Lind & Ponack

[57] ABSTRACT

Aqueous trinitrotoluene is dried by means of air which is passed through the melted trinitrotoluene by passing the melted trinitrotoluene over a porous area and forcing hot air from below through the porous area and the melted material. The porous area is preferably made of a material having a pore size of 20–50 m$\mu$.

4 Claims, 2 Drawing Figures

Fig. 1.
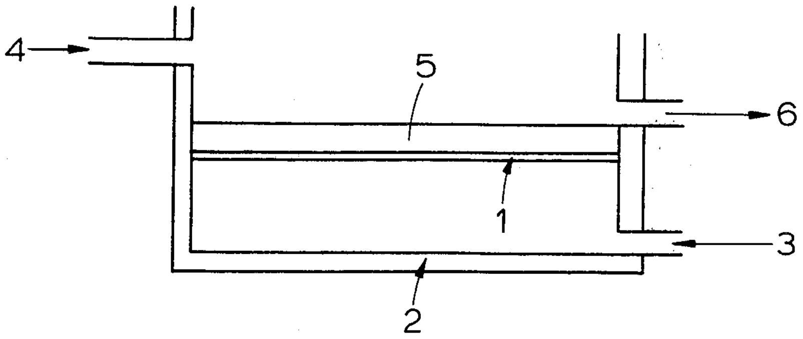
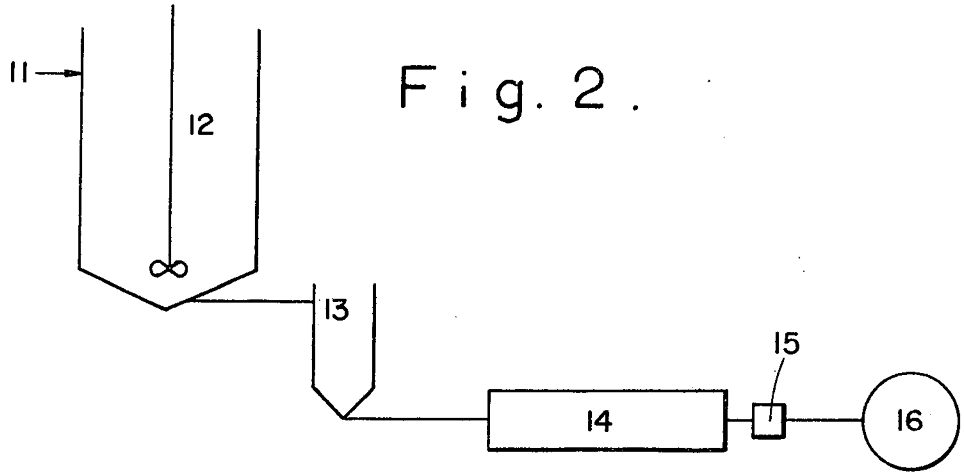
Fig. 2.

METHOD FOR DRYING TRINITROTOLUENE

BACKGROUND OF THE INVENTION

The present invention relates to an improved method for drying trinitrotoluene (TNT).

TNT is an explosive having a solidification temperature of about 80°C. It is produced either batchwise or continuously. Regardless of how it is produced, the last process step is a hot water wash of the melted TNT. After the water has been separated, the TNT contains water in minor amounts which has to be removed before the subsequent cooling (flaking).

One precautionary main principle in explosive manufacture is to keep the amount of explosive in each stage on the lowest possible level. This is performed in order to reduce the effect of a possible explosion accident. Examples in this connection are the introduction of continuous nitrating and washing processes for TNT, such as, e.g., described in Norwegian patent specification No. 93,255 and U.S. Pat. No. 3,087,971, as well as the emulsion storage of nitroglycerine.

For the drying of TNT several methods may be used. A usual method is to pass the melted TNT into an iron container equipped with a heating mantle, and to pass air through the charge through perforated tubes until the charge is free from water. Using this method may provide a concentration of several tons of TNT in the drier. Another method, which is more advantageous, especially in connection with continuous nitrating and washing processes, comprises passing the material through a vessel in a forced direction and passing air through perforated tubes into and through the material. The amount of explosives in such driers varies, but generally is in the range of about 400–600 kgs., and, thus, provides greater safety relative to batch-operations.

SUMMARY OF THE INVENTION

The object of the present invention is to lower the amount of explosives radically in comparison with previous used driers, whereby the safety during the production of explosives is enhanced.

The principle of the present invention resides in bringing the drying air and the material into a highest possible intimate contact without any dead zones and thereby reducing the drying time to a minimum. At the same time, this principle is carried out in respect of the apparatus, so that the drying process does not imply any explosion hazard. This means that, i.a., a mechanical agitation of the material has to be avoided, as well as a superheating of the apparatus and that a simple cleaning operation should be aimed at.

The process of the invention comprises passing the melted TNT through a duct the bottom of which consists of a porous material. The pore size may be varied, however, a pore size of between 20 and 50 mμ has been found suitable for this purpose. Heated air, preferably having a temperature in the range of 90–100°C, is forced through the porous bottom and the flowing material. The air pressure underneath the bottom ensures that the material does not flow through it.

The porous bottom of the duct may consist of a sintered material, such as glass or various alloys, e.g., steel or brass. The air pressure underneath the bottom area is controlled in order to provide an effervescence in the material over the entire area. Thus, in most cases the overpressure will comprise about 0.25 kg/cm$^2$.

BRIEF DESCRIPTION OF THE DRAWINGS

Other objects and features of the invention will become apparent from the following discussion, taken with the accompanying drawings, wherein:

FIG. 1 is a schematic view of a drier which may be used in the present invention; and FIG. 2 is a schematic view of a drying plant illustrating the present invention.

DETAILED DESCRIPTION OF THE INVENTION

The following non-limiting examples in which was employed an experimental drier, are given in order to illustrate the invention more in detail.

EXAMPLES 1–3

An experimental drier was employed, as shown in FIG. 1 of the enclosed drawings. The drier is equipped with a filter 1 consisting of sintered metal having a pore size of 35 mμ. It is equipped with a hot water mantle 2 through which water at 90°C is circulated. Preheated air of 90°C is passed into the compartment 3 underneath the filter 1. Melted TNT is fed into the drier through the inlet 4, flows over the filter 1, and the dried TNT flows out through the outlet 6.

The following table summarizes some results of the experiments. The solidification temperature is here used as a measure for the water content of the TNT, whereby minor amounts reduce the solidification temperature.

Three different heights of layers of TNT were used, viz., 1.5, 3.0 and 4.5 cm.

| Ex. | Height of layer cm | Drying time 0 mins. | 2.5 mins. | 5 mins. | 10 mins. |
|---|---|---|---|---|---|
| 1 | 1.5 | 76.86°C | 80.46°C | 80.49°C | 80.48°C |
| 2 | 3.0 | 76.86°C | 80.43°C | 80.49°C | 80.49°C |
| 3 | 4.5 | 76.70°C | 80.26°C | 80.33°C | 80.50°C |

Whereas in the driers of the prior art the TNT has a residence time of about 30 mins., the here performed experiments demonstrate that it is possible to reduce the residence time to about 2.5 mins. This significant reduction of the residence time could not be predicted and was only observed by the accomplished experiments.

FIG. 2 shows a production plant for the drying of TNT. In order to keep the amount of explosives at a minimum the TNT present is kept in a melted state and as an emulsion. The emulsion is not explosive.

Through the inlet 11 TNT in emulsion form is fed into the emulsion storage 12. From there it is passed through a separator 13 in which the major part of the water is removed. From the separator 13 the TNT is passed into the drier 14. The dried TNT is passed through the filter 15 to the flaker 16 where it is cooled down.

At a capacity of about 800 kgs. per hour the amount of TNT in the drier itself is about 30 kgs.

I claim:

1. A method of drying melted aqueous trinitrotoluene, said method comprising:

continuously passing a layer of melted aqueous trinitrotoluene over a porous surface while maintaining the height of said layer no more than 4.5 cm;

simultaneously forcing hot air upwardly through said porous surface and said melted trinitrotoluene thereby drying said melted trinitrotoluene; and said step of passing said melted aqueous trinitrotoluene over said porous surface being carried out at a speed such that the drying time of said melted aqueous trinitrotoluene is approximately 2.5 minutes.

2. A method as claimed in claim 1, further comprising providing said porous surface of a material having a pore size of 20–50 mμ.

3. A method as claimed in claim 1, wherein said step of passing comprises flowing said melted aqueous trinitrotoluene through a duct, the bottom of said duct comprising said porous surface.

4. A method as claimed in claim 3, further comprising providing said porous surface of a material having a pore size of 20–50 mμ.

* * * * *